(12) United States Patent
Schwartz et al.

(10) Patent No.: US 11,466,505 B1
(45) Date of Patent: Oct. 11, 2022

(54) SYSTEM FOR LIMITING EXPOSURE OF A SELECTED AREA FROM CONTAMINATED AND ADVERSE ENVIRONMENTS

(71) Applicants: Abraham Schwartz, San Juan, PR (US); Gary Woodward, McLean, VA (US); Ricardo Nieves Santiago, Bayamon, PR (US); Veronica Del Mar Diaz Rivera, Bayamon, PR (US); Abigail Toledo Rosado, Bayamon, PR (US); Jessiry Abreu Cruz, Humacao, PR (US); Paola Rodriguez Rivera, Mayaguez, PR (US); Emma Fernandez Repollet, San Juan, PR (US); Walter R. Frontera, San Juan, PR (US); Carlos Gonzalez, San Juan, PR (US)

(72) Inventors: Abraham Schwartz, San Juan, PR (US); Gary Woodward, McLean, VA (US); Ricardo Nieves Santiago, Bayamon, PR (US); Veronica Del Mar Diaz Rivera, Bayamon, PR (US); Abigail Toledo Rosado, Bayamon, PR (US); Jessiry Abreu Cruz, Humacao, PR (US); Paola Rodriguez Rivera, Mayaguez, PR (US); Emma Fernandez Repollet, San Juan, PR (US); Walter R. Frontera, San Juan, PR (US); Carlos Gonzalez, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 17/557,018

(22) Filed: Dec. 20, 2021

(51) Int. Cl.
*E05F 15/76* (2015.01)
*A61B 90/40* (2016.01)
(Continued)

(52) U.S. Cl.
CPC .......... *E05F 15/76* (2015.01); *A61B 17/3423* (2013.01); *A61B 17/3462* (2013.01);
(Continued)

(58) Field of Classification Search
CPC ....... A61G 10/00–04; A61G 11/00–009; E05F 15/76; A61B 90/40; A61B 17/3423; A61B 17/3462
See application file for complete search history.

(56) References Cited

U.S. PATENT DOCUMENTS

2016/0046130 A1* 2/2016 Burdge ................. B41J 2/1752
29/714

* cited by examiner

*Primary Examiner* — Thaddeus B Cox
(74) *Attorney, Agent, or Firm* — Hoglund & Pamias, PSC; Roberto J. Rios

(57) ABSTRACT

An access control apparatus having a protective covering configure to cover at least one of a subject or an object inside said protective covering is provided, where an opening is configured to provide access to the at least one of a subject or an object and a covering element configured to selectively cover said opening. A receiving element is provided on the protective covering and an activating device with an activating element is provided external to the protective covering. A motor is coupled to the covering element, wherein said motor selectively moves the covering element to at least partially unblock the opening based on a wireless activation signal and a distance between the activating element and the receiving element being within a predefined distance and to completely block the opening based on the wireless activation signal and the distance between the activating element and the receiving element being greater than the predefined distance, effectively limiting the exchange of contaminated or adverse environments between an internal area of the protective covering and an area outside the protective cov-
(Continued)

ering. The covering element can be an integral covering or an iris diaphragm arrangement.

31 Claims, 13 Drawing Sheets

(51) Int. Cl.
*A61G 10/00* (2006.01)
*A61B 17/34* (2006.01)
*A61G 11/00* (2006.01)
*G08C 17/02* (2006.01)
*A61B 46/10* (2016.01)
*A61B 17/00* (2006.01)

(52) U.S. Cl.
CPC .............. *A61B 90/40* (2016.02); *A61G 10/00* (2013.01); *A61G 10/005* (2013.01); *A61G 11/00* (2013.01); *G08C 17/02* (2013.01); *A61B 46/10* (2016.02); *A61B 2017/00398* (2013.01); *E05Y 2400/32* (2013.01); *E05Y 2400/66* (2013.01); *E05Y 2400/852* (2013.01); *G08C 2201/91* (2013.01)

(Iris Closed)

(Iris Opened)

(a)

(b)

(c)

- Prior Art -

- Prior Art -

- Prior Art -

SYSTEM FOR LIMITING EXPOSURE OF A SELECTED AREA FROM CONTAMINATED AND ADVERSE ENVIRONMENTS

BACKGROUND OF THE INVENTION

In general, accessing or working on an area of interest in contaminated and adverse environments can be challenging. Working on or accessing an area that is highly sensitive to such contamination poses even greater challenges where manual manipulation is necessary within the exposed area. For example, the simple act of eating and drinking in such contaminated atmospheres during a pandemic presents such challenges of limiting intake of contaminants through the nose and mouth while ingesting food or drink. This situation has been addressed in U.S. Pat. No. 11,134,729 B1 to Schwartz, et al., where a face covering such as a face mask, a face shield or a helmet contains an apparatus that activates an opening near the mouth when a fork, spoon or straw carrying an activating transponder tag, is within a designated distance of the receiver antenna of an actuating mechanism contained on the face covering. The mechanisms are controlled by the proximity of an implement carrying the tag. Other proximity activation mechanisms may involve magnetic or infrared proximity interactions. All of these mechanisms have the advantage of not requiring manual manipulation other than bringing the tagged implement within the activation range of the opening mechanism.

The contamination of atmospheric environments of concern not only include biological entities, but also toxic particulates arising from fires, volcanoes, dust storms and thermal conditions. The ability to limit exposure without the need for manual manipulation to protect a selected area from such biological agents and environmental particulates is of particular interest. For example, it would be critical to limit the time of exposure of an area of a body to contaminants while conducting emergency surgery in an open field contaminated with toxic atmospheric particulates. Thus, it would be advantageous to have a mechanism that limits exposure of the contaminants and provides direct access to the surgical area of the body only at the moments the surgical instruments are in close proximity of the surgical. In addition, there are surgical situations where it is important to maintain thermal stability for a patient by maintaining a temperature that is different from the ambient temperature of an operating area. For example, in the United States, an operating room is held at approximately 70-75° F., and in Britain the temperature is held at approximately 65-70° F. While these temperatures may not impose a significant stress for an adult patient, they are considered a significant stress for pediatric patients. Thus, the ability to maintain a temperature closer to the body temperature of an infant (98.6° F.) while still having access to the surgical area could reduce complications, thereafter.

A cleanroom is provided in situations where a product needs to be manufactured within certain quality requirements. A cleanroom is an engineered space, which maintains a very low concentration of airborne particulates. It is well isolated, well-controlled from contamination, and actively cleansed. Such rooms are commonly needed for scientific research, and in industrial production for all nanoscale processes, such as semiconductor manufacturing. A cleanroom is designed to keep everything from dust to airborne organisms, or vaporized particles, away from it, and so from whatever product is being handled inside it. On the other hand, a cleanroom can also help keep materials escaping from it. This is often the primary aim in hazardous biology and nuclear work, in pharmaceutics and in virology.

Thus, what is needed is an apparatus and a system that provides controlled access to an area of interest by limiting or eliminating the flow of airborne particulates between areas of interest without manual manipulation.

SUMMARY OF THE INVENTION

Normally for surgery in a modern hospital, the patient is completely draped with sterile material leaving the area for operation open throughout the procedure. However, such pristine conditions do not exist when preforming emergency surgery in an open field under conditions of atmospheric contamination. The area of the body normally chosen for surgery would have a RF tag activation apparatus that would cover the area and would open only when one or more the surgical instruments are within the activation range of the mechanism and closed when tagged instruments are out of the activation range of the mechanism.

In the case of pediatric surgery in a hospital operating room where a higher temperature would be beneficial for the patient, a specific temperature is maintained under the surgical draping. An apparatus over the area for surgery and would open only when the tagged surgical instruments were within the activation range and would otherwise be closed to help maintain the specified temperature under the surgical drape.

According to another aspect of the invention, the release of contaminated agents from contaminated patients into the immediate environment of the surgeons is minimized. This is particularly applicable when performing surgery on patients contaminated with airborne biological agents.

According to another aspect of the invention, direct access to an isolated area is provided to perform specific manipulations while limiting the period of exposure to the area.

BRIEF DESCRIPTION OF THE DRAWINGS

Further features and advantages of the invention will become apparent from the following detailed description taken in conjunction with the accompanying figures showing illustrative embodiments of the invention, in which.

Figure 1:
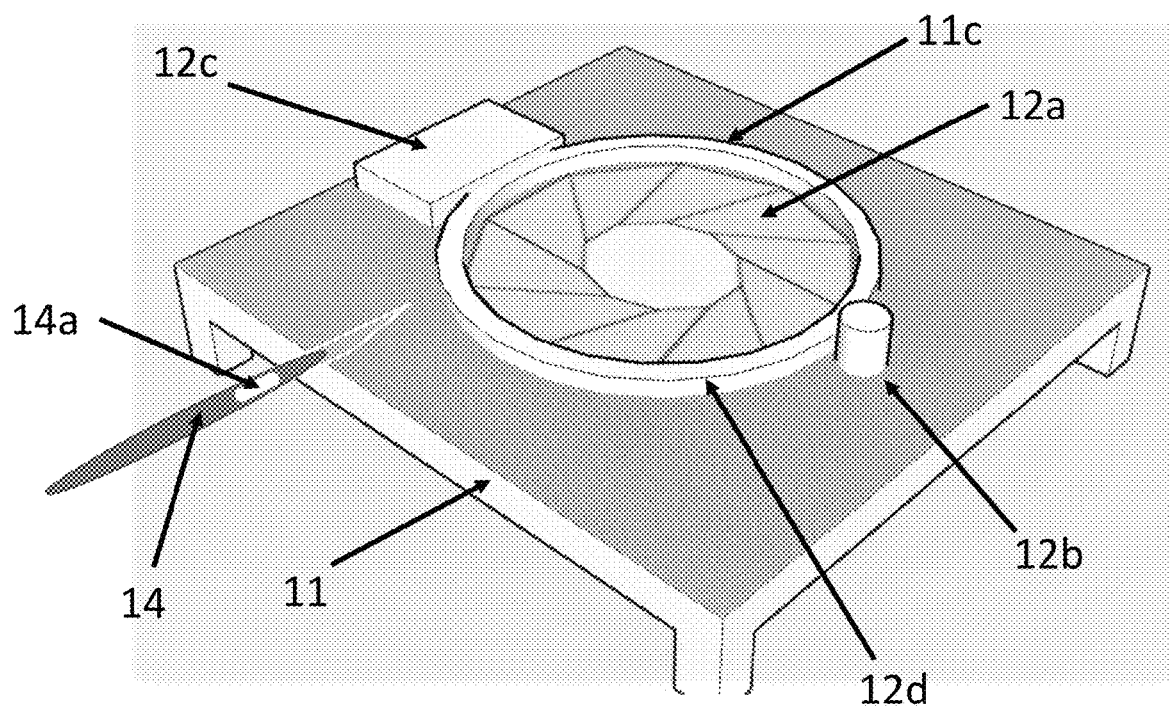
FIG. 1 shows an access control apparatus, according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The present invention provides an apparatus and a system including a mechanism that physically opens and closes over an area of interest when an activating device (such as but not limited to a tool or instrument) which is external to the area of interest, comes within the proximity of the area of interest.

According to an embodiment of the invention, this can be performed by a motor that selectively moves a covering element in front of and away from an opening that provides access to the area of interest, as described in U.S. Pat. No. 11,134,729 B1 to Schwartz, et al. (herein after the '729patent), the content of which is incorporated herein by reference in its entirety. A brief non-limiting explanation of the apparatus, system, and mode of operation disclosed in the '729 patent will be discussed below. However, it is to be understood that the complete explanation (including disclosure not literally disclosed herein) is found in the '729 patent, which was previously incorporated herein in its entirety.

The '729 patent describes a protection equipment comprising a protective covering, for the nose and the mouth of a person, that includes a mouth opening provided on a front area of the protective covering and positioned in front of the mouth of the person. A covering element is provided to selectively cover the mouth opening in the protective covering. The covering element comprises a material impervious to airborne contaminants and is large enough and provided close enough to the mouth opening such that it can block airborne contaminants from entering inside the protective covering. The cover element is coupled to a moving mechanism that mechanically moves the covering element to selectively block and at least partially unblock the mouth opening.

Moreover, the moving mechanism can move the covering element linearly or rotationally in relation to the mouth opening. According to an embodiment disclosed by the '729 patent, the moving mechanism is a servomotor with an output shaft coupled to the covering element that will be rotationally moved in relation to the mouth opening when the output shaft of the servomotor rotates in a clockwise or counterclockwise direction to selectively block or at least partially unblock the mouth opening. According to another embodiment, the moving mechanism is a servomotor with an output shaft having a linear actuator coupled to the covering element that will be linearly moved in relation to the mouth opening when the output shaft of the servomotor rotates in a clockwise or counterclockwise direction to selectively block or at least partially unblock the mouth opening. Thus, the covering element can be moved horizontally, vertically or diagonally in relation to the mouth opening. The servomotor and all the circuitry, processors, or modules needed to carry out the invention can be powered by a battery (e.g., rechargeable, replaceable, condenser, etc . . . ). The protective covering disclosed in the '729 patent is provided with the receiving element which is connected to a processing module. An output of the processing module is connected to the moving mechanism that has an output shaft coupled to the covering element. The activating device is provided with an activation element configured to wirelessly interact with an equipment receiving element provided on the protective covering in order to control movement of the moving mechanism. The activating device can be a utensil or a person wearable device. Thus, the activation element can be integrated or removably coupled to anything that will be in proximity to a person's mouth while a person is eating or drinking. For example, the activation element can be part of a removable label/sticker that can be affixed to a utensil, or the activation element can be provided with a fixing element such as but not limited to a hook and loop fastener for removably fasten the activation element to the utensil. Also, the activation element can be integrally formed with the utensil as a one-piece activating device. According to another disclosed embodiment, the activation element is provided on a device wearable by the person. The wearable device includes at least the activation element and any circuitry necessary to carry out the method of the invention. The activation element on the wearable device also interacts with the equipment receiving element to block or at least partially unblock the mouth opening. The wearable device can be a device wore by the person on the hand such as but not limited to a glove, a wristband, a watch, smartwatch, a bracelet or a ring.

In operation, the activation element generates a wireless activating signal that is received by the receiving element when the activation element is within a predefined distance d from said receiving element. Also, the generated wireless activating signal can be received by the receiving element independent of the distance between the receiving element and the activation element. In an embodiment of the invention, the receiving element is a radio-frequency identification (RFID) transceiver module provided on the protective covering and the activation element is a RFID tag that transmit a RFID signal. A Near-Field Communication (NFC) tag/transceiver arrangement can also be used, especially for short or limited communication distances. One important aspect of the invention is that the activating device used by the person needs to be associated with the protective covering worn by the person. In addition, the system of the invention can distinguish between situations where the mouth opening can be partially unblocked (e.g., using a straw) and situations where the mouth opening must be completely unblocked (e.g., using a fork). For example, this can be accomplished by providing an ID to utensils that require complete unblocking of the mouth opening and a different ID to utensils that only require partial unblocking of the mouth opening. The receiving element can recognize the different IDs and the moving mechanism will be actuated to selectively move the covering element to either partially unblock or completely unblock the mouth opening based on the ID signal received.

The present invention proposes a mechanism based on a mechanical iris to ensure that the covering element does not interfere with the area around large openings during operation.

According to an embodiment of the present invention shown in FIG. 1, an access control apparatus (10) includes a covering element (12) having a plurality of iris leaves (12a) that are coupled to a motor (12b). The covering element (12) is provided to block or at least partially unblock an opening (11c) provided on a support base (11). A receiving element includes an antenna (12d) and a controller (12c) that is connected to the motor (12b). According to the embodiment of the invention, the antenna (12d) is positioned around the covering element (12). However, it is to be understood that the antenna (12d) can be positioned at other places on the access control apparatus (10), or more than one antenna (12d) can be used, as long as the quality and integrity of the wireless signals being transmitted and/or received is not affected. According to the invention, an activating element (14a) is provided on an activating device (14) that is external to the access control apparatus (10). FIG. 1 shows the controller (12c) and the motor (12b) mounted on the support base (11). However, as will be explained below, at least one of the controller (12c) or the motor (12b) can also be integrated into said covering element (12).

The basic operating principle according to an embodiment of the present invention will be explained in conjunction to FIGS. 1, 2a, 3a and 3b and the disclosure of the '729 patent.

The covering element (12) will keep the opening (11c) blocked as long as no RFID/NFC activation signal is received by the RFID/NFC antenna (12d)/controller (12c) provided on the access control apparatus (10) and the distance between the RFID/NFC tag (14a) and the antenna (12d)/controller (12c) is greater than a predefined distance d. Once the RFID/NFC tag (14a) is in proximity to the access control apparatus (10) within the predefined distance d, an RFID/NFC activation signal is transmitted by the RFID/NFC tag (14a) and received by antenna (12d)/controller (12c). According to this embodiment, the antenna (12d)/controller (12c) transmits an interrogation signal that is received and read by a passive RFID/NFC tag (14a) provided on the activating device (14) when the activating device (14) is in proximity to the access control apparatus (10) within the predefined distance d. As a consequence, the RFID/NFC tag (14a) transmits the RFID/NFC activation signal to the antenna (12d)/controller (12c) where a processing module will determine whether a partial or complete unblocking of the opening (11c) is required based on the information contained in the RFID/NFC activation signal. The RFID/NFC activation signal can either contain an ID associated to a complete unblocking situation or a partial unblocking situation. Once the processing module determines if a partial or complete unblocking of the opening (11c) is required, an output of the processing module selectively actuates the motor (12b) which will in turn move the iris leaves (12a) to at least partially expose the area of interest through the opening (11c). This allows a person to comfortably insert the activating device (14) inside the area of interest and to remove the activating device (14) out of the area of interest when desired. Then, once the activating device (14) is outside the predefined distance d and the RFID/NFC activation signal is no longer received at the antenna (12d)/controller (12c), the processing module selectively actuates the motor (12b) which will in turn move the iris leaves (12a) in an opposite direction to completely cover the opening (11c). It is also envisioned, that when the iris leaves (12a) are moved to unblock the opening (11c), a delay timer (with a fixed or configurable duration) can be started to maintain the iris leaves (12a) in the unblocked position and to automatically have the motor (12b) move the iris leaves (12a) back to the blocked position once the delay timer is over. As can be appreciated, positioning an activating device (14) without an activating element within the distance d will not cause the iris leaves to move since no RFID/NFC activation signal is present.

For the purpose of the invention, a partial unblocking means that the motor is selectively controlled to move the iris leaves from either an unblocked position or a completely blocked position and deliberately stop moving the motor at a position that partially unblocks the opening (11c).

Figure 2A:
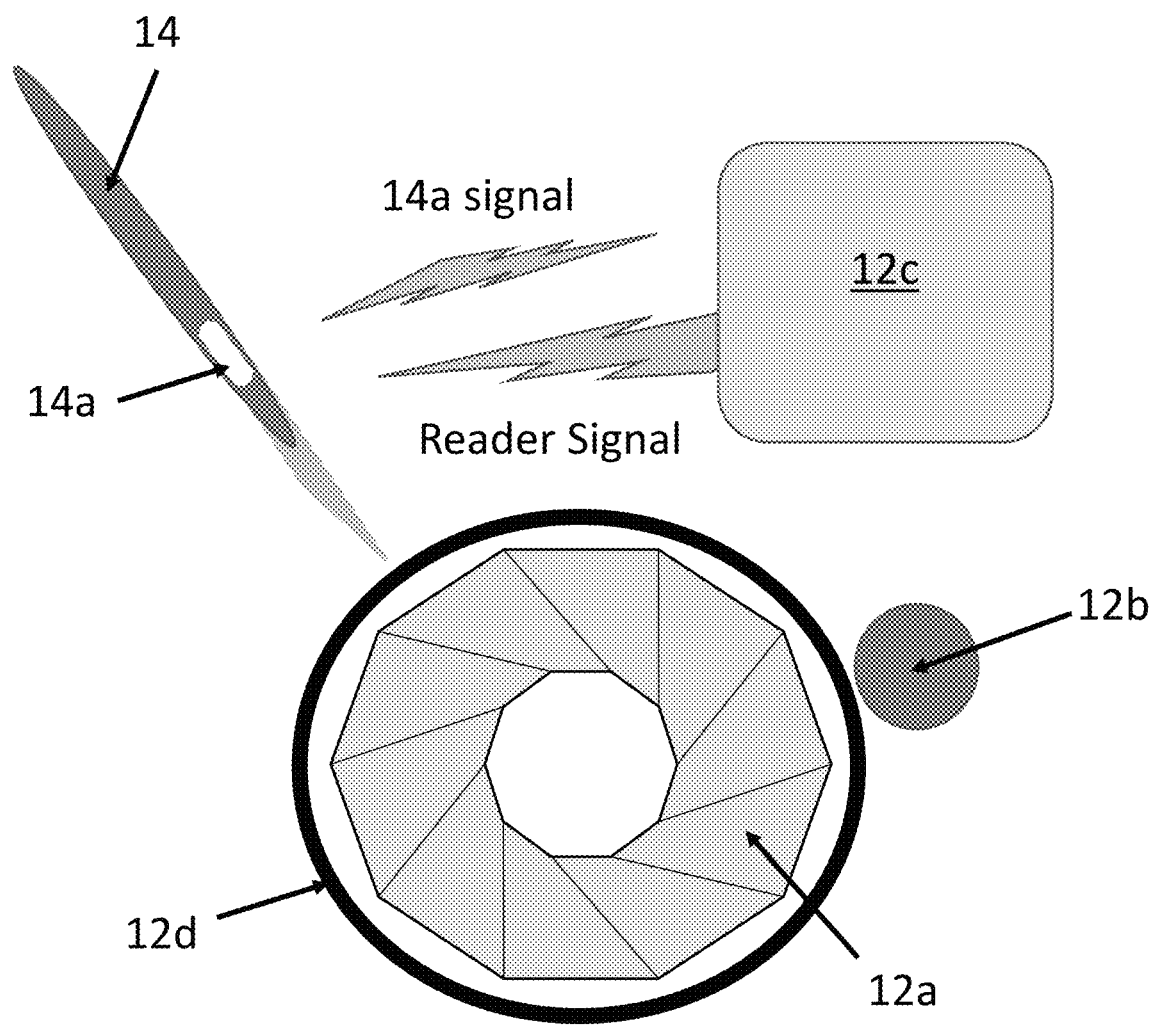
FIG. 2a illustrates the radio signals communication between the receiver sending out a reader signal and the transponder of the tagged instrument sending back an activation signal, according to the present invention.
Figure 2B:
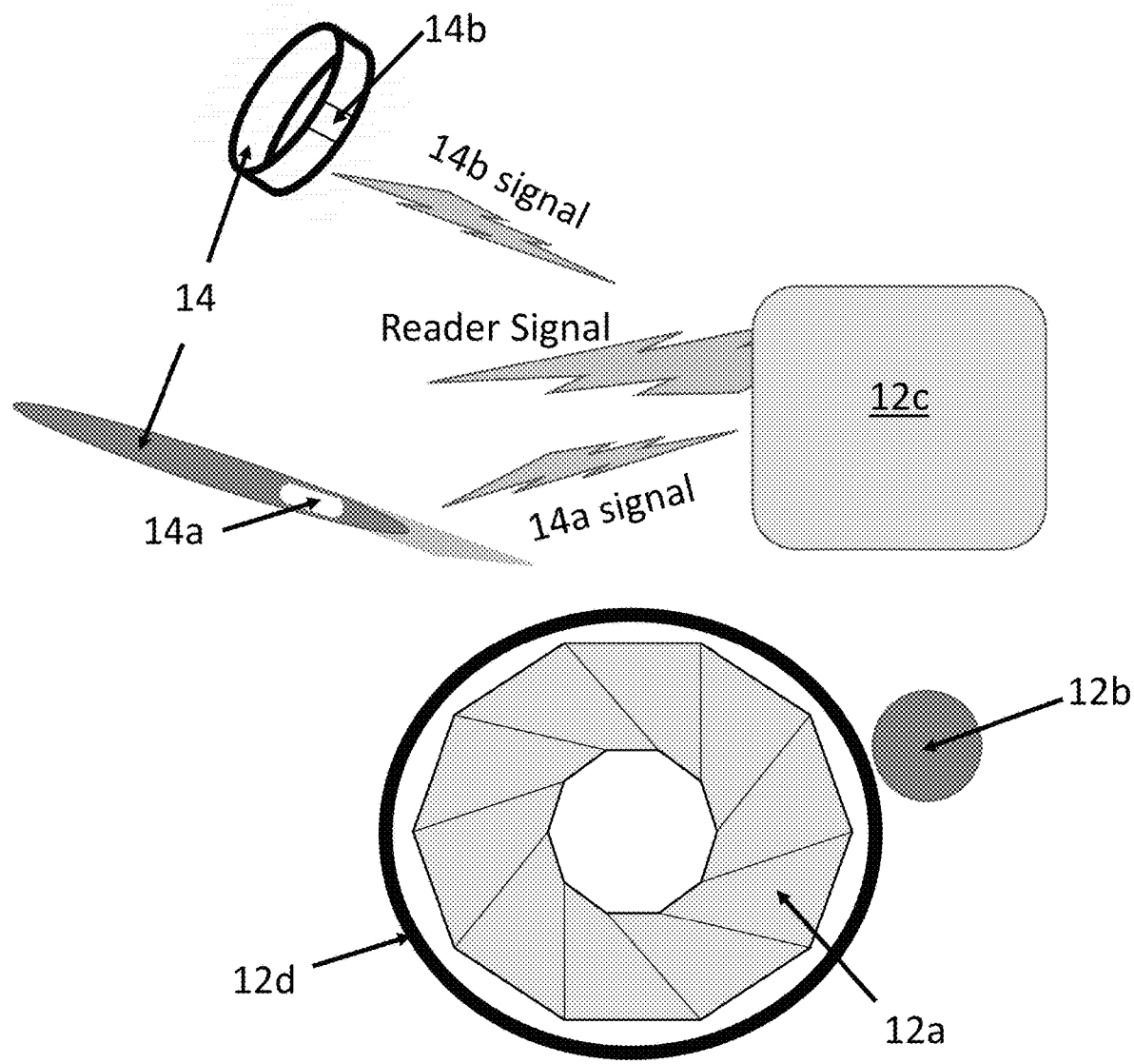
FIG. 2b illustrates the radio signals communication between the receiver sending out a reader signal and the transponders of the plural tagged instruments sending back activation signals, according to the present invention.
Figure 3A:
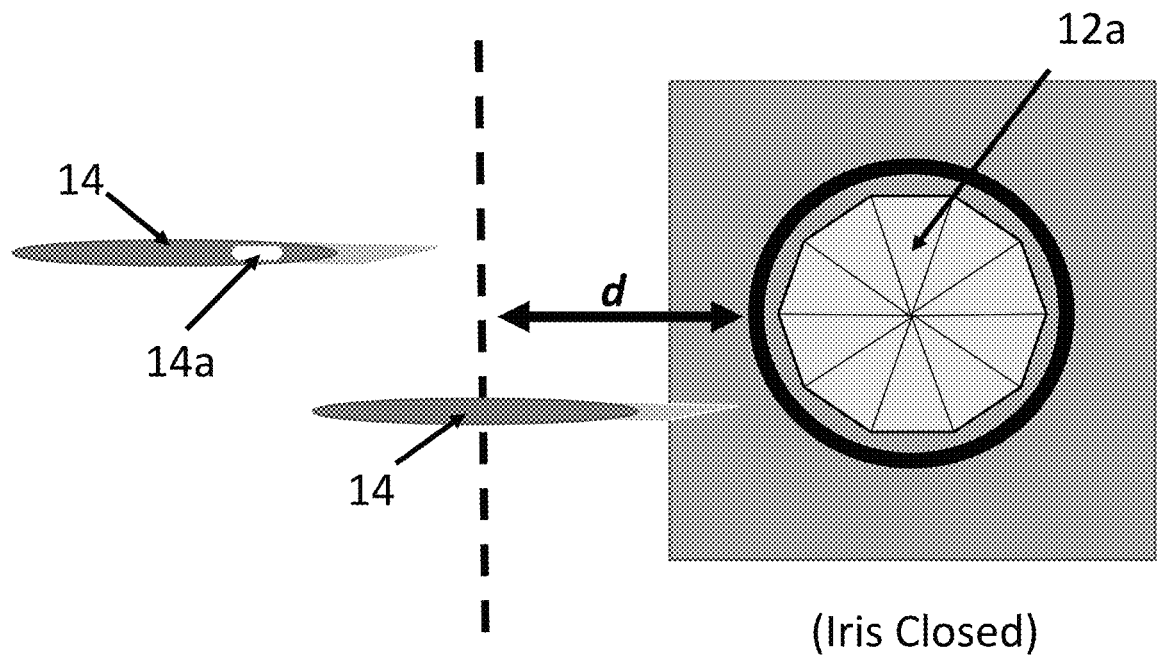
FIGS. 3a-3b illustrate the actuation of the invention where a tagged scalpel has not entered the critical distance and has not detected the reader signal of the electronics and where a tagged scalpel has entered the critical distance, detected the reader signal and has sent the tag signal back to activate the iris opening through a set of gears connecting the iris mechanism and the iris motor, according to the present invention.
Figure 3B:
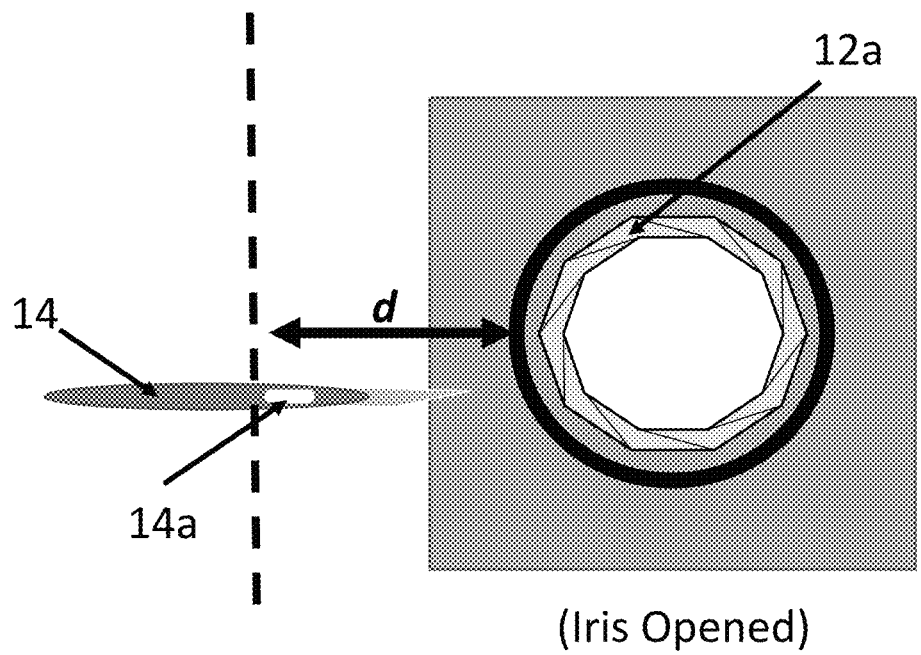

FIG. 2b illustrates a scenario where more than one RFID/NFC activation signal is required to move the iris leaves into an at least partially unblocked position. For example, an activation device such as a wearable bracelet (14) having an activating element (14b) can be assigned to a specific surgeon so that only that specific surgeon is authorized to operate on a subject such a patient using the surgical instrument (14) having the activating element (14a). Once both the activating element (14a) on the surgical instrument (14) and the activating element (14b) on the wearable bracelet (14) are in proximity to the access control apparatus (10) within the predefined distance d, RFID/NFC activation signals are transmitted by the RFID/NFC activating element (14a) and the activating element (14b) and received by antenna (12d)/controller (12c). According to this example, the antenna (12d)/controller (12c) transmits respective interrogation signals that are received and read by the activating element (14a) and the activating element (14b) when the surgical instrument (14) and the wearable bracelet (14) are in proximity to the access control apparatus (10) within the predefined distance d. As a consequence, the activating element (14a) and the activating element (14b) transmits the respective RFID/NFC activation signals to the antenna (12d)/controller (12c) where a processing module will determine if the surgeon using the surgical instrument (14) is authorized and whether a partial or complete unblocking of the opening (11c) is required based on the information contained in the RFID/NFC respective activation signals. Once the processing module determines that the surgeon is authorized and if a partial or complete unblocking of the opening (11c) is required, an output of the processing module selectively actuates the motor (12b) which will in turn move the iris leaves (12a) to at least partially expose the area of interest through the opening (11c).

Typically, RFID/NFC tags share a common communication channel and if several tags attempt to send information at the same time, the reader will be unable to distinguish these signals causing a tag collision problem. Simultaneous responses from numerous tags prevent the reader from correctly translating the signal, which decreases throughput since no tag is aware of the activity of any other tag, and so they cannot prevent the simultaneous transmission of tags. To minimize tag collisions, RFID readers must use an anti-collision protocol. Each anti-collision protocol uses certain multi-access methods for identification in order to physically separate the transmitters' signals. Accordingly, they can be categorized into four different types: Space Division Multiple Access (SDMA), Frequency Division Multiple Access (FDMA), Code Division Multiple Access (CDMA) and Time Division Multiple Access (TDMA). It is known that in an RFID environment, anti-collision protocols typically use the TDMA method and protocols that use this method first select an individual tag from a large group using a specific algorithm and then the communication takes place between the selected tag and the reader. Significant increases in number of collisions in the identification process decreases the throughput and increases the number of transmitted bits. These protocols can be divided into three categories: Aloha-based protocols, tree-based protocols and hybrid protocols (which use a combination of the first two methods). Some anti-collision protocol that can be used are explained in detail by: Nikola Cmiljanic et al., A Comparison of RFID Anti-Collision Protocols for Tag Identification, *Appl. Sci.* 2018, 8, 1282; Zang et al., A Fast RFID Tag Anticollision Algorithm for Dynamic Arrival Scenarios Based on First-Come-First-Serve, *Hindawi-Mobile Information Systems*, Volume 2019, Article ID 4625758, 17 pages; and Bang et al., Efficient Novel Anti-collision Protocols for Passive RFID Tags—Three methods for fast tag identification: bislotted tree based RFID tag anti-collision protocols, query tree based reservation, and the combining method of them, *Auto-ID Labs*, White Paper WP-HARDWARE-050, March 2009. It is to be understood that the specific anti-collision protocol needed to avoid tag collision is not part of the invention and any anti-collision protocol of the prior art can be used as long as both RFID tags can be simultaneously or sequentially read in accordance with the teachings of the present invention. Alternatively, multiple RFID readers can be provided to read multiple RFID tags, where reader collision is avoided by implementing an anti-collision protocol according to the prior art.

Figure 12:
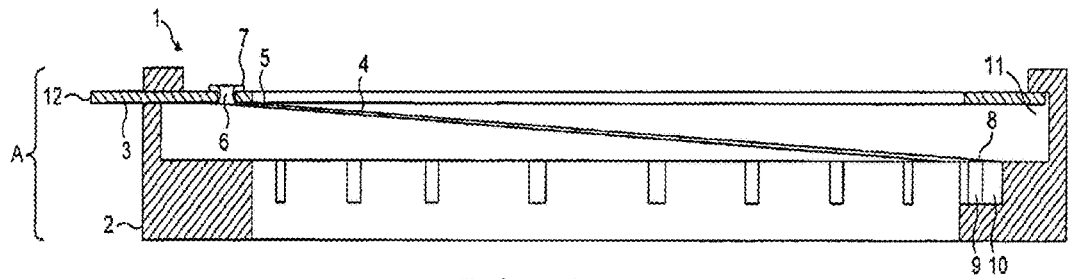
FIGS. 12-14 show an iris diaphragm arrangement of the prior art.
Figure 13:
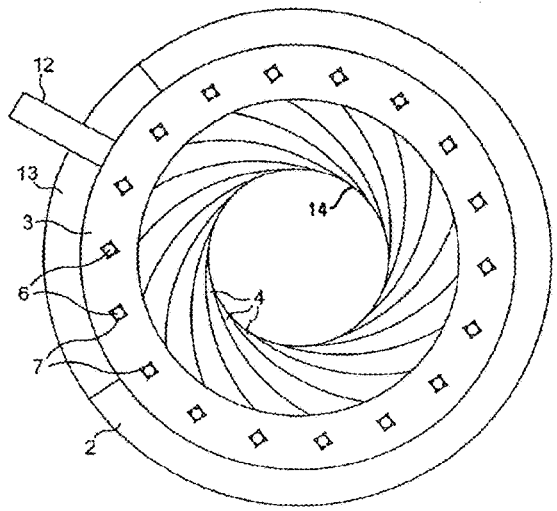
Figure 14:
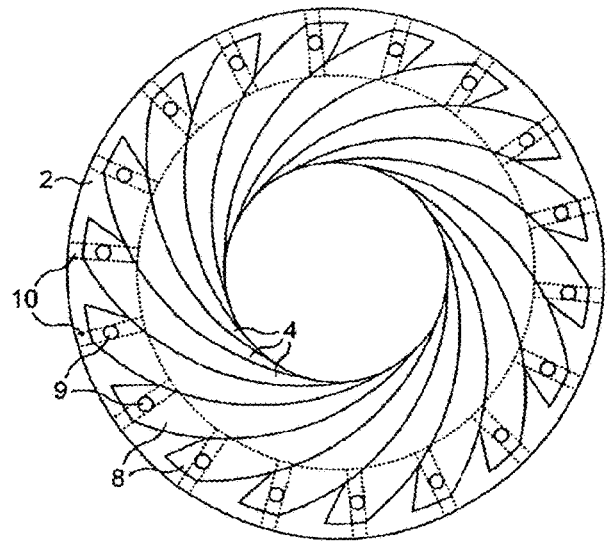

The covering element (12) according to an embodiment of the invention, comprises a well-known iris diaphragm arrangement having a plurality of overlapping curved leaves (12*a*) mounted in a circle around an aperture (11*c*), which can be rotated in unison to adjust the accessible diameter of the aperture (11*c*). The iris diaphragm comprises a base provided with an aperture, a rotatable element provided with a corresponding aperture, and a plurality of curved leaves (12*a*), one end of which are mounted in a fixed pivotal position to one of the element or base, and the other end of which are mounted in a sliding pivotal position to the other of the element or base. The leaves are mounted at equal points around the circumference of the aperture and are so shaped that the curve along their inner edge corresponds to the curvature of the aperture, so when they are in the fully retracted position the aperture is unobstructed. When the element or the base is rotated the leaves are rotated about their fixed pivot and cross over the aperture between and fully blocked position, partially unblocked position, and a fully unblocked position. One example of an iris diaphragm of the prior art that can be used according to the present invention, is the one disclosed on U.S. Pat. No. 6,912,097 B2 to Woods, the contents of which is incorporated herein by reference in its entirety, where an iris diaphragm 1 comprises a base 2, a rotatable disc 3 and a number of leaves 4 (only one leaf shown in FIG. 12). A first end 5 of the leaf 4 is rotatably attached to an opening 6 provided in the disc 3, by means of a burst hole joint 7. A second end 8 of the leaf 4 is provided with a pin 9 which is positioned in a slide 10, which is provided in the base 2. As shown in FIG. 13, the disc 3 is provided with eighteen apertures 6 (although other number of apertures can be used based on the number of leaves), one for each of the eighteen burst hole joints 7 on each of the overlapping leaves 4. Accordingly, as shown in FIG.14 the base 2 (the outline of which is shown in broken lines) is provided with eighteen slides 10 (although other number of slides can be used based on the number of leaves), and each leaf 4 is provided with a pin 9, which is positioned in one slide 10. The disc 3 is positioned in a slot 11 (as shown in FIG. 12) provided in the base 2, and it is provided with an operating handle 12, positioned in a further slot 13 (as shown in FIG. 13) provided in the base 2. When the disc 3 is rotated by the handle, the end 5 of each leaf 4 is drawn in a circular direction by the joints 7. The joints 7 also rotate on their own axis due to the second ends 8 of each leaf 4 being positioned in the stationary slides 10. As a result of the above-described action, each pin 9 is moved along each slide 10. In the movement from fully retracted to fully advanced, each pin moves first towards the center of the iris aperture 14, then back in the opposite direction as the joints 7 follow their circular course. The leaves 4 are so shaped that the above-described actions result in the iris aperture 14 closing. The aperture can be opened, or placed in any desired position, by the positioning of the handle 12. Iris diaphragm 1 is provided with a narrow width, Distance A, due to the narrow width of the burst hole joints 7 and the pin 9 and slide 10 mechanisms. It will be appreciated that Distance A is restricted only by the capacity to machine the pin 9 onto the leaf 4. The width of the iris diaphragm 1 is determined by size of pin 9 which can effectively be attached to the leaf 4. The handle 12 is connected to an operating means, for example an electric motor, which can be electronically controlled. It is to be understood that the specific iris diaphragm arrangement is not part of the invention, and any iris diaphragm of the prior art can be used as long as the leaves can be selectively moved by a controlled motor in accordance with the teachings of the present invention. According to an embodiment of the invention, the iris leaves (12*a*) are transparent so that the operational area of interest is visible whether the opening is open or closed.

According to a preferred embodiment of the invention, the motor (12*b*) is a servomotor. However, it also envisioned that other type of motors can be used to selectively move the iris leaves (12*a*). By way of not limiting examples, the motor (12*b*) can be an AC brushless motor, a DC brushed motor, a DC brushless motor, a direct drive motor, a linear motor, or a stepper motor.

According to an embodiment of the invention, a motor (12*b*) is coupled to said iris diaphragm via a mechanical shaft that selectively rotates the iris leaves (12*b*). However, it is also envisioned that the motor (12*b*) can selectively move the iris leaves (12*a*) via a non-contact coupling such as, but not limited to, a magnetic shaft coupling that uses a magnetic field instead of a physical mechanical connection to transmit torque from one shaft to another. It is non-contact and utilize attraction and repulsion of the magnetic poles to transmit rotational power. Non-contact synchronous couplings have a softer start and stop function than most standard couplings and can be used as a torque limiting device since there are no mechanically engaged parts. It can be used to linearly, horizontally, vertically, diagonally or rotary move the covering element (12) in relation to the opening (11*c*) either in the form of a single covering element or in the form of an iris diaphragm covering element. Essentially, the motor is provided with a magnetic shaft that is magnetically coupled to a magnetic shaft of the mechanism (e.g., the handle 12 of U.S. Pat. No. 6,912,097 B2 to Woods explained above) that moves the iris leaves so that forward and reverse rotation of the magnetic shaft of the motor causes rotation of the magnetic shaft of the mechanism that moves the iris leaves to block or at least partially unblock the opening (11c).

Figure 4:
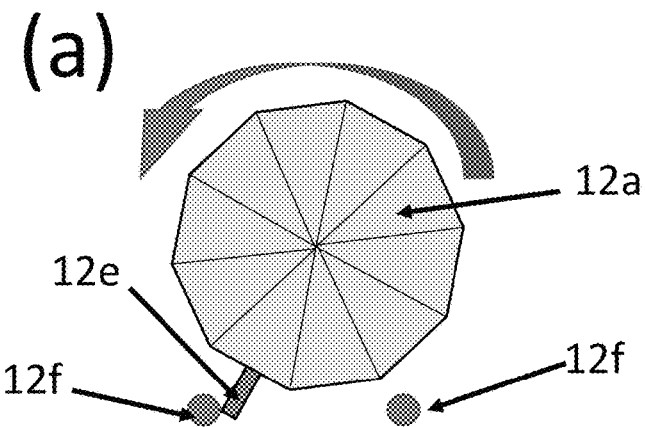
FIG. 4 shows a mode of opening the orifice with the iris motor and limiting the degree of rotation using stop relays to position the iris leaves, where the iris is closed by reversing the positive and negative polarity of the motor poles, according to the present invention.
Figure 4:
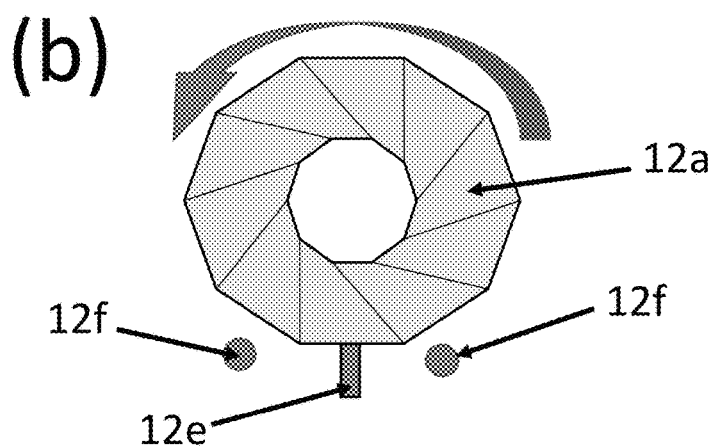
Figure 4:
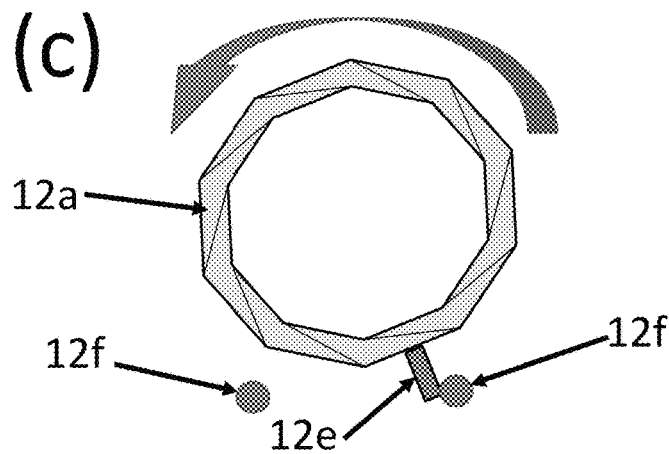

FIG. 4 illustrates one mode of operation according to an embodiment of the invention, where an iris ring of the covering element is rotated back and forth by an element (12e) geared to a motor that uses relays (12f) to stop the motion of the iris leaves by breaking the electrical connection at specific points of travel in both directions, blocked position (a), partially unblocked position (b), and completely blocked position (c).

Figure 5:
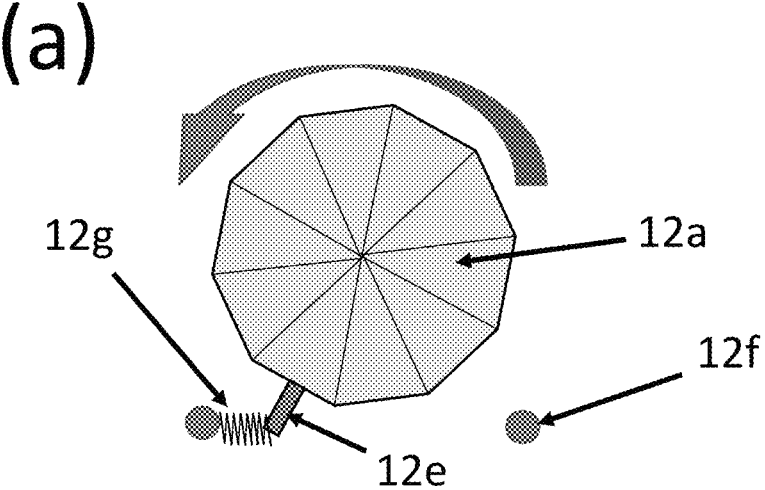
FIG. 5 shows a mode of opening the iris where the motor is operated electrically to open the orifice and the iris is closed by spring tension when the electricity to the motor is interrupted.
Figure 5:
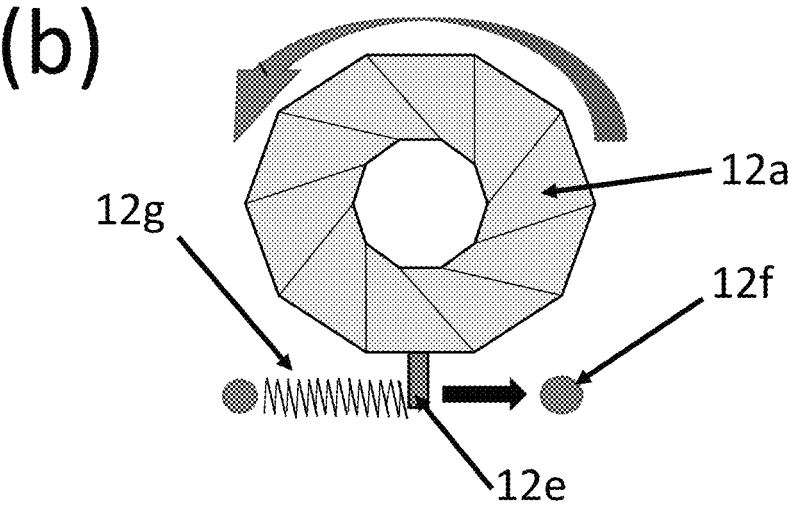
Figure 5:
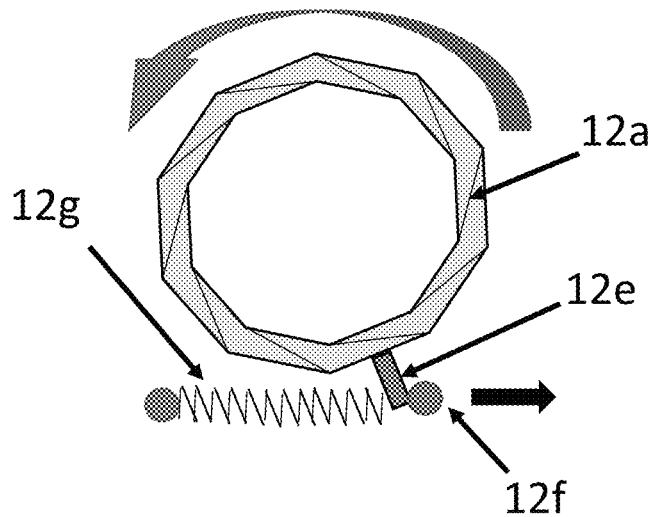

FIG. 5 illustrates another mode of operation according to an embodiment of the invention, where a single electronic relay (12f) is used stop the movement of the iris leaves (12a) at the maximum point of opening and a mechanical spring (12g) to return the iris to the completely closed position.

Figure 6A:
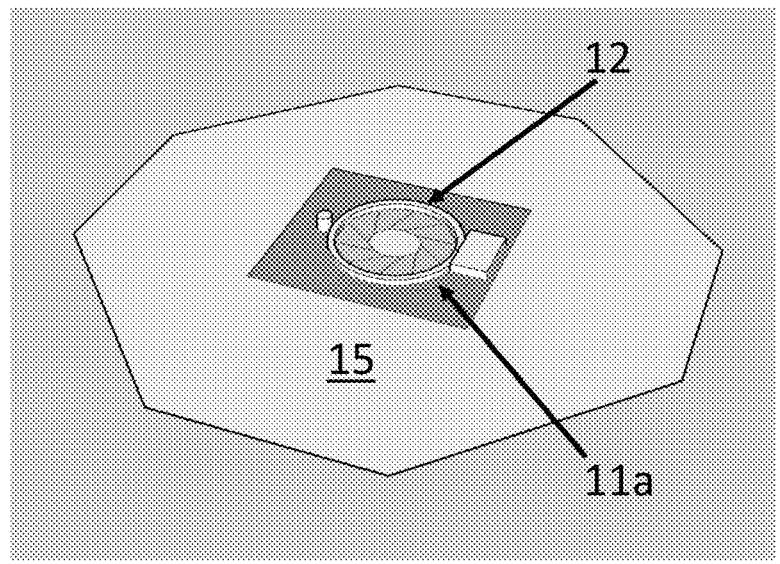
FIGS. 6a-6b illustrate the top and bottom of the iris apparatus with a draping material attached to the supporting structure, according to the present invention.
Figure 6B:
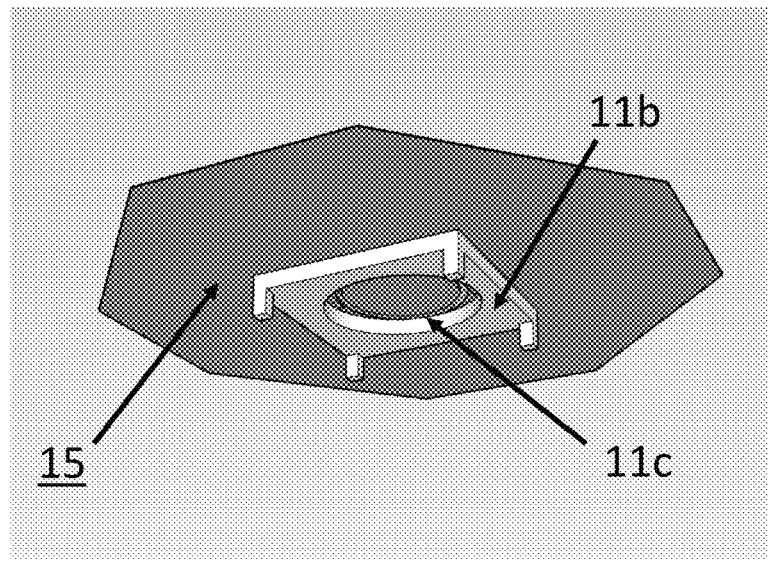

FIGS. 6a and 6b illustrate an embodiment of the invention where the access control apparatus (10) is coupled to a covering (15) such as but not limited to a drape configured to cover at least a body part of a subject such as a patient located within the area of interest. As can be appreciated, the support base (11) and the drape (15) are coupled so that an upper surface (11a) of the support base (11) and an upper surface of the iris leaves (12a) are accessible to a person and a lower surface (11b) of the support base (11) along with a lower surface of the drape (15) are not accessible to a person. In a preferred embodiment of the invention, the support base (11) includes a plurality of support legs to provide sufficient working space between the patient's body part and the opening (11c) such that there is no physical contact between the access control apparatus (10) and the body and the operational areas outside of the opening (11c) must be covered, if not sealed, to prevent contamination entering under the covering drape (15). The drape (15) can be integrally formed with the access control apparatus (10) or alternatively, the drape (15) can be removably attached to the access control apparatus (10) by any known attaching means such as but not limited to: an adhesive element, hook and loop element and/or a magnetic arrangement so long as the attaching means maintains the required environment isolation to the area of interest. For the purpose of the invention, a subject can be a human patient or an animal patient. Moreover, the drape (15) can cover only an area to be treated or operated on the patient or alternatively can cover the entire body of the patient. The edges of the drape (15) can be adhered to the body or an area surrounding a body part of the patient. When thermal stability is required to operate at temperatures higher than used in the normal operating room, the material covering the opening can have low thermal conductivity and the inner surface of the draping (5) can be thermally reflective. The drape (5) can also be sealed to a non-heat conducting operating table. It is envisioned that an elevated temperature can be provided by introducing regulated warmed air under the drape (5) through sterilized HEPE filters.

Figure 7:
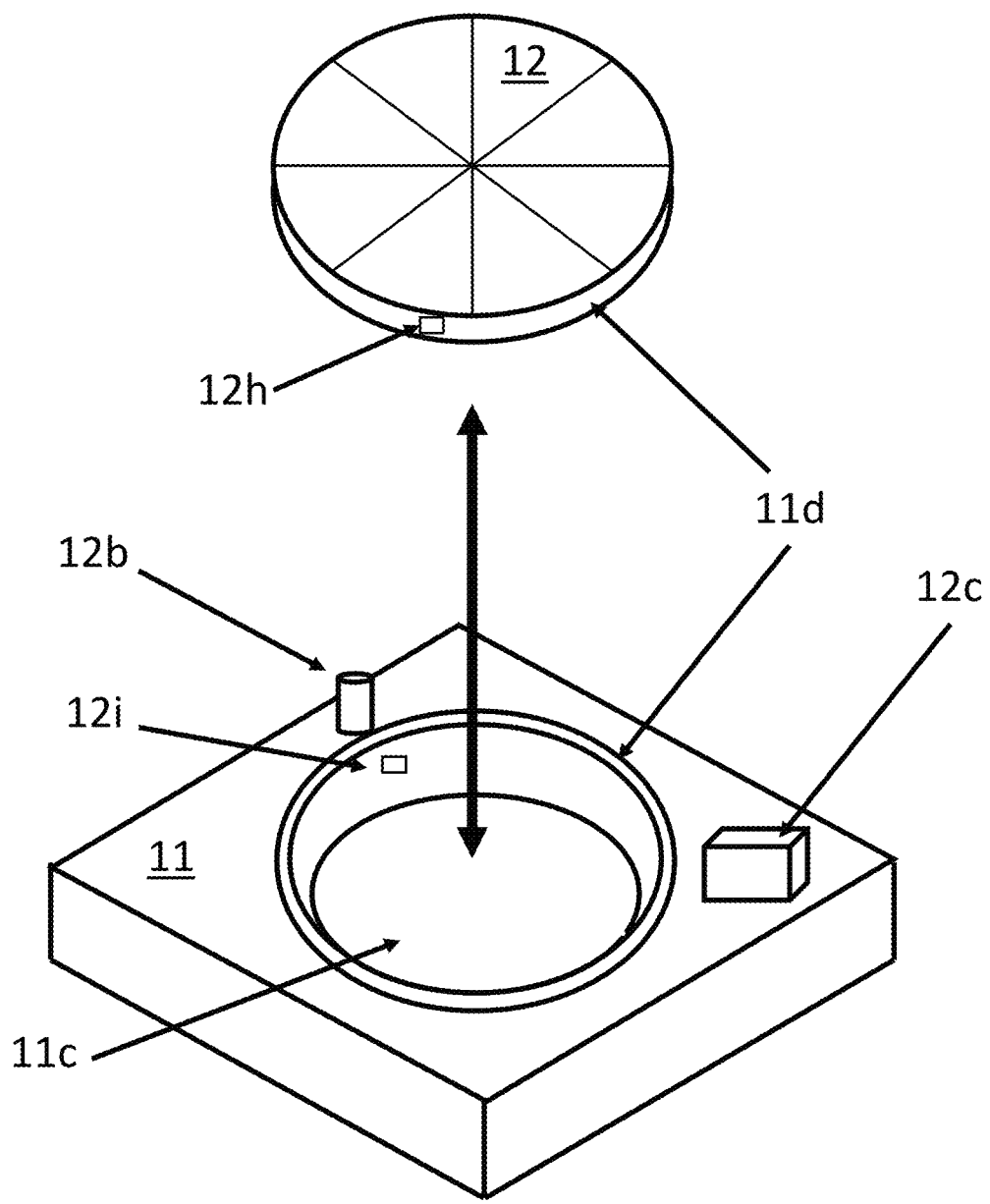
FIG. 7 illustrates the covering element being removable from the support base, where the motor and the receiver are provided on the support base, according to the present invention.
Figure 8:
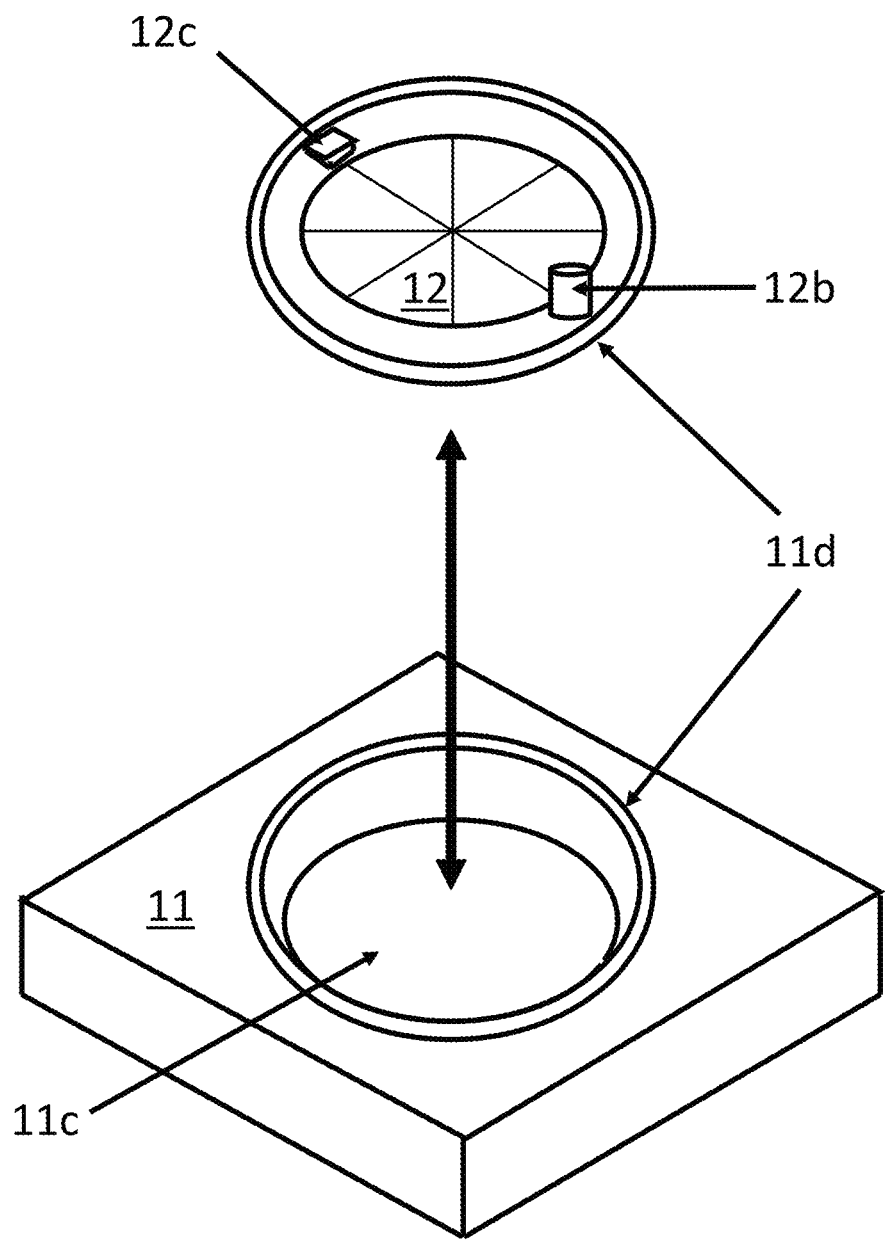
FIG. 8 illustrates the covering element being removable from the support base, where the motor and the receiver are provided on the covering element, according to the present invention.

FIGS. 7 and 8 show an embodiment of the access control apparatus (10) where the covering element (12) is removably attached to the support base (11). Specifically, the covering element (12) is securely attached to the access control apparatus (10) through a sealing arrangement (11d) between the covering element (12) and the opening (11c). For example, an O-ring can be provided on an outer surface of the covering element (12) or on a surface of the opening (11c) such that a friction fit sealing arrangement is provided between the covering element (12) and the opening (11c) when the covering element (12) is inserted inside the opening (11c). Alternatively, one magnet can be provided covering element (12) and another magnet can be provided on the opening (11c) so that the covering element (12) is attracted to the opening (11c) with a sufficient attraction force so that a sealing arrangement is created between the surfaces of the covering element (12) and the opening (11c). It is to be understood, that any equivalent sealing arrangement can be used as long as the covering element (12) is securely attached to the opening (11c) while ensuring a proper seal between them.

As shown in FIG. 7, the motor (12b), the antenna (12d) and the controller (12c) are provided on the support base (11) so that the element (12e) that selectively rotates the iris leaves (12a) is coupled to the shaft of the motor (12b) when the covering element (12) is inserted into the opening (11c). As previously explained, this coupling can be done by a physical coupling or a non-contact coupling between the element (12e) and a mechanical shaft of the motor (12b). Alternatively, the motor (12b), the antenna (12d) and the controller (12c) can be provided on the covering element (12), as shown in FIG. 8.

Figure 9:
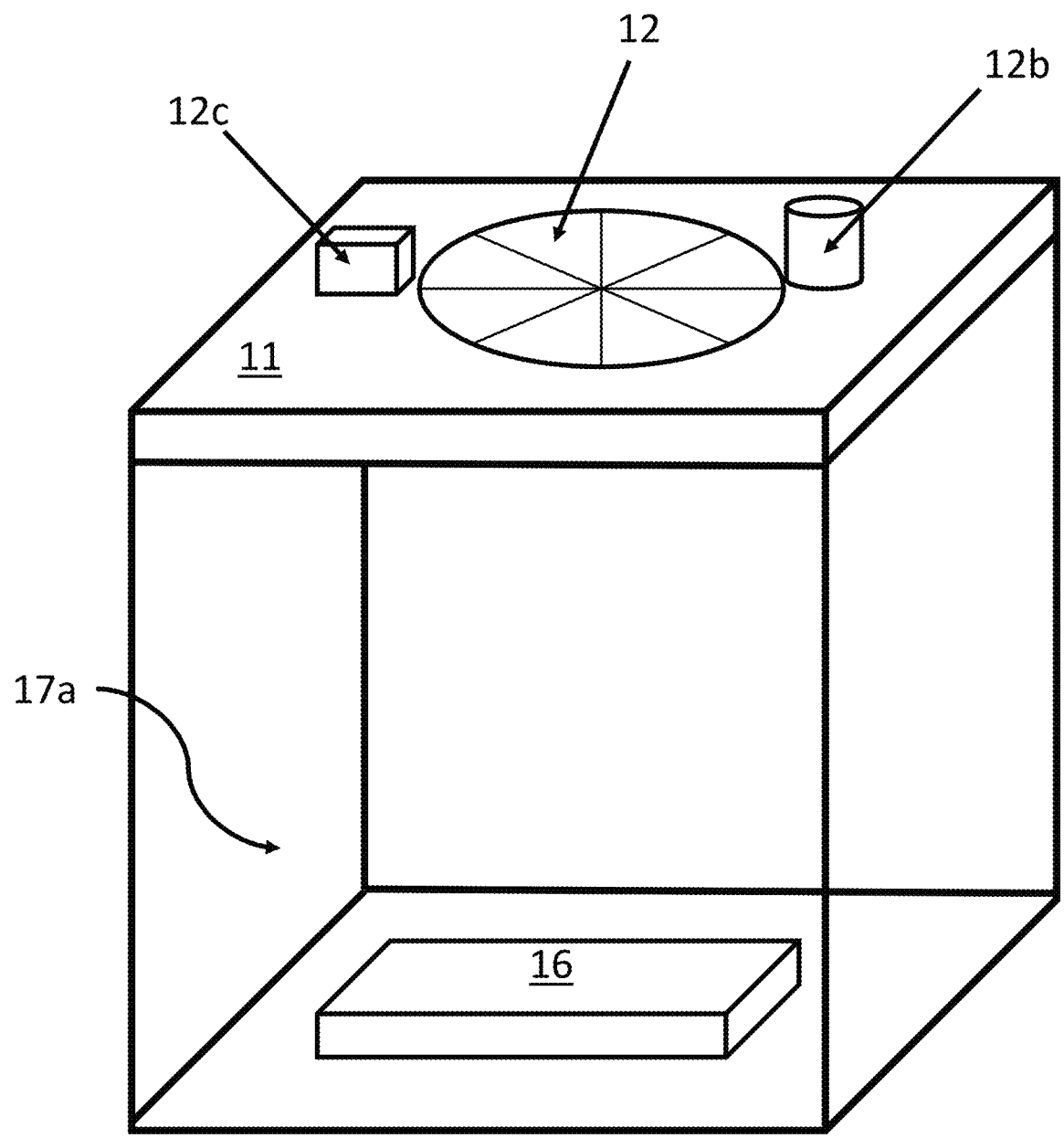
FIG. 9 illustrates the access control apparatus provided on a housing enclosing an object, according to the present invention.
Figure 10:
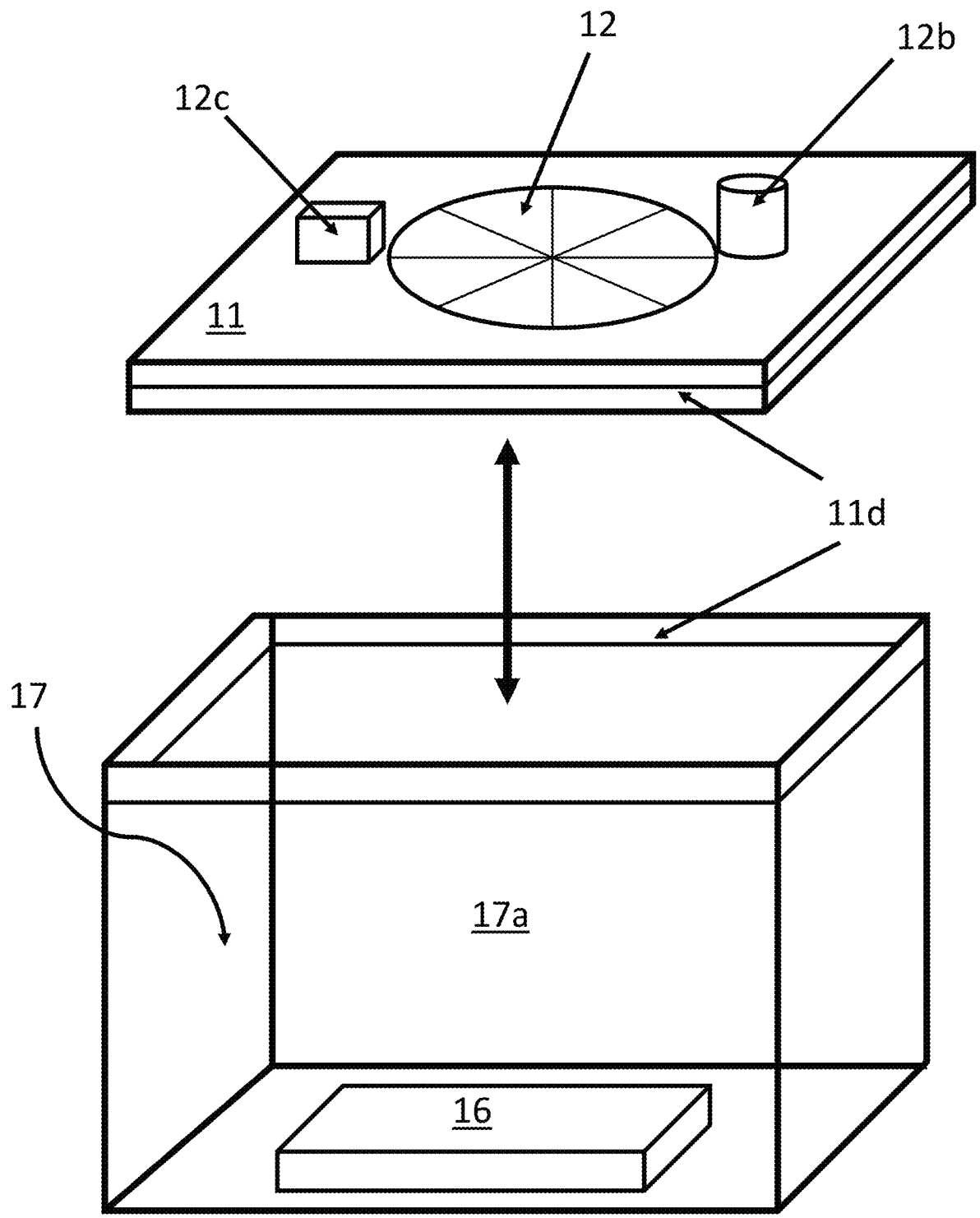
FIG. 10 illustrates the access control apparatus being removable from the housing enclosing the object, according to the present invention.
Figure 11:
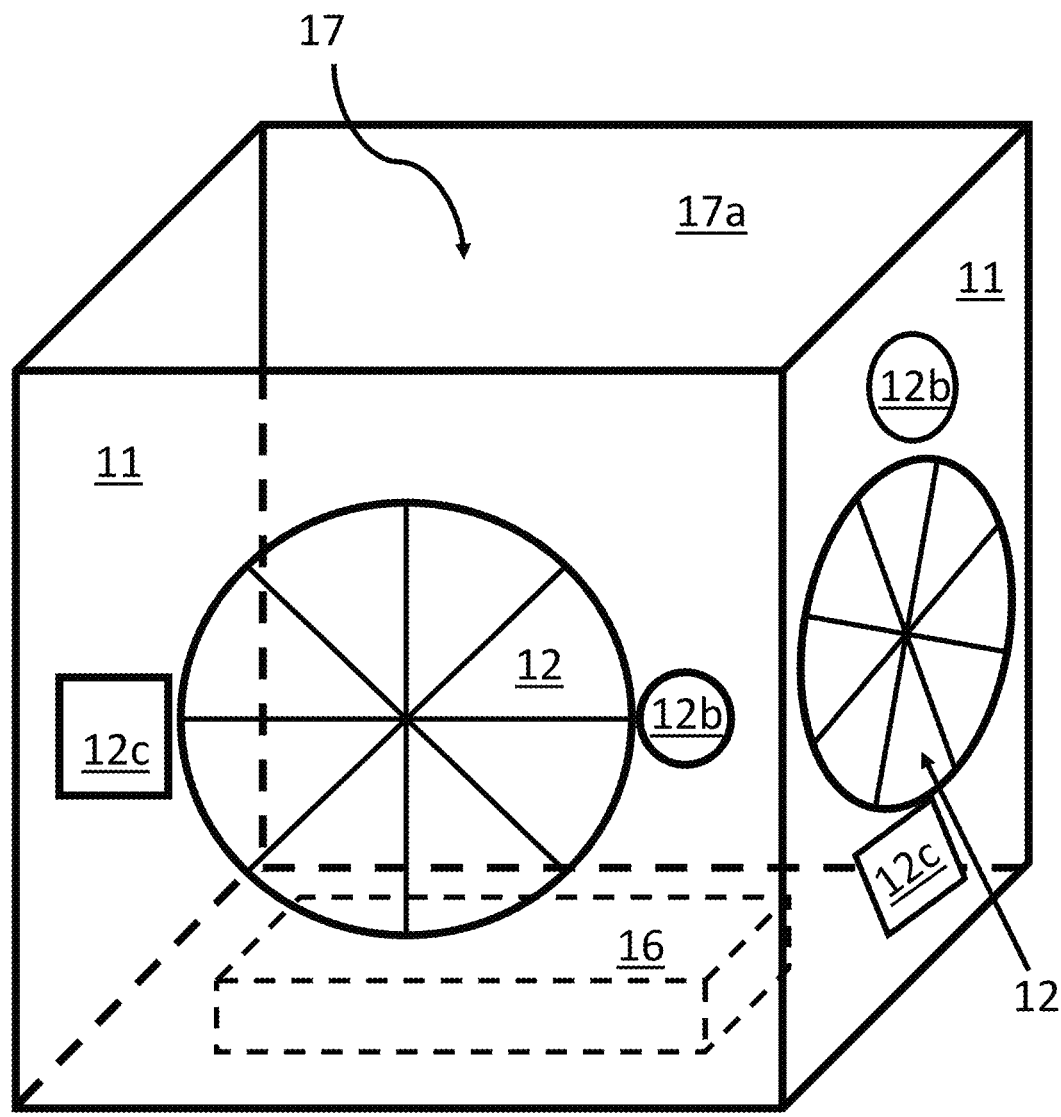
FIG. 11 illustrates the access control apparatus being provided on at least one wall of the housing enclosing the object, according to the present invention.

FIGS. 9-11 show an embodiment where an object (16) is enclosed inside an area of interest inside a housing (17). For the purpose of the invention, a housing and/or a protective covering refer to elements and structures such as boxes or covers provided to cover subjects or objects enclosed in relatively small areas of interest and are not considered to be larger structures such as for example a residence or a room. According to one embodiment, the object (16) is placed inside the housing (17) and the access control apparatus (10) is positioned to close an upper opening of the housing (17), as shown in FIG. 9. It is envisioned that the housing (17) includes at least one wall (17a) being transparent. The same sealing arrangement (11d) previously explained can be provided between an outer edge of the access control apparatus (10) and an inner surface of the upper opening of the housing (17). Alternatively, the access control apparatus (10) can be integrally formed with the housing (17), where a lower opening is provided so that the housing (17) is positioned over said object (16). In this embodiment, a sealing element such as, but not limited to, a rubber element can be provided along the periphery of the lower opening so that a seal is created between the housing (17) and a surface where the housing (17) is placed. It is also envisioned that an access control apparatus (10) according to the invention can be provided on at least one side wall (17a) of the housing (17), as shown in FIG. 11, where at least one wall (17a) of the housing (17) is transparent.

For the purpose of the invention, an object can be organisms such as but not limited to plants that need to be protected against contamination from airborne particles, e.g., pollen. In addition, an object can be for example an apparatus such as but not limited to a microscope having a sample that needs to be isolated and free from contaminants. An object can also be an article of such as but not limited to a watch, jewelry, miniature circuity, a semiconductor wafer or a pharmaceutical substance or pill. According to an embodiment of the invention, an activating device can also be a manufacturing tool such as but not limited to a robot arm, or any other manual tool used by an operator to work on the object.

Some examples where the present invention can be implemented will be discussed.

Emergency Field Surgery

A sterile surgical field pack is provided containing the access control apparatus with the iris mechanism mounted on the support base, the drapes, and the tagged surgical instruments. The access control apparatus is positioned over the operating area and the drape is positioned to cover the immediate area around the wound such that the wound is isolated from the battlefield contamination. The surgical instruments carry a radio transponder tag that when positioned within a specified distance from the access control apparatus causes the iris to open allowing the surgeon access to the wound, and the iris closing when a tagged instrument is withdrawn beyond the distance. This mechanism limits exposure of the wound to battlefield contamination during times of non-active surgery.

Surgery on Contaminated Patients

Conducting surgery on a patient infected with a highly contagious airborne contaminant directly exposes the surgeon to the contaminant. The present invention provides an extra level of protection over the normally provided by standard protective gear by limiting the period of direct exposure by closing off the area of active surgery when the tagged instruments are out of the critical range of the iris opening.

Thermal Regulation of Surgical Procedures

Performing surgery on infants at 65-70° F. places an unnecessary thermal stress on them. To address this, the drape of the present invention has a heat reflecting component on the underside and the ambient temperature under the drape is maintained with regulated warm HEPE filtered air source introduced under the drape to keep the ambient temperature for the infant between 75-85° F. The thermal stability of ambient air is improved by limiting the period of access to the surgical area by opening only when tagged instruments are used on the patient.

Repair of Delicate Mechanisms or Electric Circuit Boards

Repairing delicate mechanisms, such as a watch, on a workbench exposes the mechanism and parts to particulate airborne contamination. The present invention, while performing the repair and construction of delicate objects, limits the exposure of the mechanism to airborne contamination to periods of active manipulation with tagged tools such that the access occurs only when the tools are within the critical distance of the iris.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. A system for limiting exposure of a selected area of interest from contaminated and adverse environments, the system comprising:
   a protective covering configured to cover at least one of a subject or an object inside said protective covering, said protective covering including an opening configured to provide access to said at least one of a subject or an object and a cover configured to selectively block said opening;
   a wireless signal receiver provided on said protective covering and a wireless signal transmitter provided on an activating device external to said protective covering; and
   a motor coupled to said cover, wherein said motor selectively moves said cover to at least partially unblock said opening based on a wireless activation signal and a distance between said wireless signal transmitter and said wireless signal receiver being within a predefined distance and to completely block said opening based on the wireless activation signal and the distance between said wireless signal transmitter and said wireless signal receiver being greater than said predefined distance, effectively limiting an exchange of contaminated or adverse environments between an internal area of said protective covering and an area outside said protective covering.

2. The system of claim 1, wherein said motor moves said cover to completely unblock the opening when said wireless signal transmitter is within said predefined distance.

3. The system of claim 1, wherein said opening remains at least partially unblocked for a predefined amount of time.

4. The system of claim 1, wherein said opening remains at least partially unblocked as long as said wireless activation signal is received by said wireless signal receiver.

5. The system of claim 1, wherein said activating device is a surgical instrument.

6. The system of claim 1, wherein said activating device is a wearable device configured to be worn by a person.

7. The system of claim 5, wherein said activating device comprises a manufacturing tool.

8. The system of claim 6, wherein said wearable device is a glove, a wristband, a watch, smartwatch, a bracelet or a ring.

9. The system of claim 1, wherein said protective covering further includes a drape configured to cover at least a body part of the subject located inside said protective covering.

10. The system of claim 1, wherein said cover is removably coupled to said protective covering.

11. The system of claim 1, wherein said opening is provided on a support base.

12. The system of claim 11, wherein said cover is removably attached to said support base.

13. The system of claim 12, wherein said wireless signal receiver and said motor are provided on said cover.

14. The system of claim 12, wherein said wireless signal receiver and said motor are provided on said support base.

15. The system of claim 1, wherein said motor linearly moves said cover in relation to said opening.

16. The system of claim 1, wherein said motor rotatably moves said cover in relation to said opening.

17. The system of claim 1, wherein said wireless signal receiver comprises a RFID transceiver and said wireless signal transmitter comprises a RFID tag that transmits said wireless activation signal so that the motor moves said cover to at least partially unblock the opening when said wireless activation signal is received by said RFID transceiver.

18. The system of claim 1, wherein said wireless signal receiver comprises a RFID transceiver and said wireless signal transmitter comprises a RFID tag that transmits said wireless activation signal so that the motor moves said cover to completely block the opening when said wireless activation signal is not received by said RFID transceiver.

19. The system of claim 1, wherein said wireless activation signal is a radio frequency (RF) signal.

20. The system of claim 1, wherein said wireless signal receiver comprises a first magnet and said wireless signal transmitter comprises a second magnet so that the motor moves said cover to at least partially unblock the opening when said wireless activation signal is a magnetic signal received by said first magnet.

21. The system of claim 1, wherein said wireless signal receiver comprises a first magnet and said wireless signal transmitter comprises a second magnet so that the motor moves said cover to completely block the opening when said wireless activation signal is a magnetic signal not received by said first magnet.

22. The system of claim 1, wherein said wireless signal receiver comprises an infrared (IR) sensor and said wireless signal transmitter comprises an IR light source that transmits said wireless activation signal so that said motor moves the cover to at least partially unblock the opening when said wireless activation signal is an IR signal received by said IR sensor.

23. The system of claim 1, wherein said wireless signal receiver comprises an infrared (IR) sensor and said wireless signal transmitter comprises an IR light source that transmits said wireless activation signal so that said motor moves the cover to completely block the opening when said wireless activation signal is an IR signal not received by said IR sensor.

24. The system of claim 1, wherein said wireless signal transmitter is removably coupled to said activating device.

25. The system of claim 1, wherein said motor is physically coupled to said cover through a shaft.

26. The system of claim 1, wherein said motor is coupled to said cover through a non-contact coupling.

27. The system of claim 26, wherein said non-contact coupling is magnetic.

28. The system of claim 1, wherein said protective covering further includes a housing configured to enclose said object located within said protective covering.

29. The system of claim 28, wherein said cover is at least one of removably attached to said housing or integrated into a wall of said housing.

30. The system of claim 1, wherein said cover comprises a plurality of leaves forming an iris diaphragm.

31. The system of claim 30, wherein said plurality of leaves are simultaneously moved by said motor to either completely block said opening or at least partially unblock said opening.

* * * * *